United States Patent

Okamoto

Patent Number: 5,616,139
Date of Patent: Apr. 1, 1997

[54] METHOD AND APPARATUS FOR OPERATING A CORNEA

[76] Inventor: Shinseiro Okamoto, 31-19, Ookayama 1-Chome, Meguro-ku, Tokyo 152, Japan

[21] Appl. No.: 256,547
[22] PCT Filed: Nov. 19, 1993
[86] PCT No.: PCT/JP93/01699
§ 371 Date: Jul. 20, 1994
§ 102(e) Date: Jul. 20, 1994
[87] PCT Pub. No.: WO94/12131
PCT Pub. Date: Jun. 9, 1994

[30] Foreign Application Priority Data

Nov. 20, 1992 [JP] Japan .................................. 4-333857
Dec. 10, 1992 [JP] Japan .................................. 4-352194
Dec. 15, 1992 [JP] Japan .................................. 4-353741
Feb. 3, 1993 [JP] Japan .................................. 5-037277

[51] Int. Cl.$^6$ ................................. A61F 9/00; A61N 5/00
[52] U.S. Cl. ................................................ 606/4
[58] Field of Search ......................... 606/4, 5, 6; 604/22, 604/23, 24, 294, 297, 298, 300, 301, 302

[56] References Cited

U.S. PATENT DOCUMENTS

| | | |
|---|---|---|
| 3,769,963 | 11/1973 | Goldman et al. . |
| 4,326,529 | 4/1982 | Doss et al. . |
| 4,623,337 | 11/1986 | Maurice . |
| 4,718,418 | 1/1988 | L'Esperance, Jr. . |
| 4,820,264 | 4/1989 | Matsui et al. .......................... 604/294 |
| 4,994,058 | 2/1991 | Raven et al. . |
| 5,009,660 | 4/1991 | Clapham ............................... 604/294 |
| 5,108,412 | 4/1992 | Krumeich et al. ....................... 604/294 |

FOREIGN PATENT DOCUMENTS

| | | |
|---|---|---|
| 0218427 | 4/1987 | European Pat. Off. . |
| 0331082 | 9/1989 | European Pat. Off. .................. 606/4 |
| 62-101247 | 5/1987 | Japan . |
| 1274759 | 11/1989 | Japan . |
| WO89/06519 | 7/1989 | WIPO . |
| WO92/01430 | 2/1992 | WIPO . |

*Primary Examiner*—Angela D. Sykes
*Assistant Examiner*—Sonya Harris Ogugua
*Attorney, Agent, or Firm*—Foley & Lardner

[57] ABSTRACT

Method and apparatus of operating the cornea by using an ultraviolet laser, such as an excimer laser, for correcting an abnormal curvature of the cornea, such as myopia, hyperopia, and astigmatism, or for treating opacity of the cornea, uses a cooling device for cooling the cornea before, during, or after the operation, or all three. A liquid medicine for promoting healing is sprinkled or sprayed onto the cornea using a sprinkling device, which can be incorporated in the cooling device. A laser beam is irradiated after the excess liquid medicine is removed from the cornea using a suction device, which can also be incorporated in the cooling device. Due to the cooling of the cornea and the medicine application, the undesirable side effects from a photochemical reaction of the laser beam can be reduced.

36 Claims, 11 Drawing Sheets

METHOD AND APPARATUS FOR OPERATING A CORNEA

TECHNICAL FIELD

This invention relates to a method of operating on the cornea of an eye for correcting an abnormal curvature thereof, such as myopia, hyperopia and astigmatism, or for treating opacity of the cornea, and also relates to an apparatus therefor.

BACKGROUND ART

For correcting an abnormal curvature of the cornea of an eye, such as myopia, hyperopia and astigmatism, or for treating opacity of the cornea, it is known to surgically remove portions of the cornea by rubbing it with a spatula-like scalpel, or by grinding it with a rotating file. However, in the case of using such a spatula-like scalpel or a file, drawbacks have been encountered in that it has been difficult to accurately form the optical axis of the eye since the eyeball moves during the operation. Thus, the cornea operation could not be performed smoothly and neatly, and satisfactory results could not be expected. Further, much time has been required for the curing the cornea after the operation. Alternatively, there is already known a method of operating on the cornea using a laser knife, as disclosed for example, in U.S. Pat. No. 4,718,418 and U.S. Pat. No. 4,994,058. However, even with this lease operation method, there have been problems associated with using a laser that adversely affects the cornea. Specifically, the laser generates and intense photochemical hear, which attacks the tissue of the cornea, so that after the operation, the cornea is liable to undergo a tissue destruction, a burn, alternation, distortion, opacity and so on and much time is required for the curing after the operation.

To solve these problems, an operation on the cornea has now been conducted using an ultraviolet laser, particularly an excimer laser, which is said to curtail the effects of photochemical heat among lasers; however, even with the excimer laser, the effects due to a photochemical thermal reaction can not be entirely avoided.

When ablating the tissue of the cornea with an excimer laser, the molecules of the cornea are cut, and this is called ablation. When the excimer laser is applied to the cornea, many free radicals are produced with the ablation, and also it is thought to produce the following phenomenon occurs. The moisture in the corneal stroma is dissipated as steam upon laser beam radiation, and also is heated to a temperature of 200~300° C. to be formed into bubbles in the cornea, and moves actively to destroy the arrangement of collagen in the corneal stroma. Further, the excimer laser beam, when impinging on the collagen, cuts the bond of the molecules thereof to produce a plume (mushroom-shaped cloud) to produce a local thermal imbalance condition, thereby generating a high temperature of 1000° C. This high temperature diffuses to the neighborhood cells to impart a thermal equilibrium condition to the cornea in the vicinity of the laser beam-irradiated portion, thereby causing a temperature rise of about 15° C. as a whole to impart a thermal trouble to the corneal stroma, which creates the cause of the opacity. Furthermore, when the excimer laser beam is applied to the cornea, an impact sound is produced, and a high pressure impulsively develops. As described above, even if the excimer laser is used, the temperature of the cornea rises, and the arrangement of the collagen of the cornea is destroyed, and stresses due to the pressure increase are applied to the cornea, and particularly opacity develops immediately beneath the surface layer of the cornea. Thus, these side effects can not be avoided. Also, a collagen-like material is secreted from the endothelial cells to Descemet's membrane.

It is an object of this invention to provide a method of operating the cornea of an eye by the use of an ultraviolet laser, in which the side effects caused by the photochemical thermal reaction can be suppressed as much as possible.

Another object of the invention is to provide an apparatus that can be effectively used for the above operation.

DISCLOSURE OF THE INVENTION

A method of operating the cornea of an eye according to the present invention comprises the steps of cooling an operation-applying portion of the eye cornea to suppress a photochemical thermal effect and also to lower the activity of cells of the cornea; sprinkling or spraying a liquid medicine, having such effects as cornea remedy, cure promotion and resolution, onto the cornea at predetermined times before, during and after the operation; separating the epithelium of the cornea; and removing the excess liquid medicine on the cornea, and applying an ultraviolet laser beam to the operation-applying portion.

Apparatus for operating the cornea of an eye according to the present invention comprises an ultraviolet laser beam source; control means for controlling an ultraviolet laser beam emitted from the laser beam source; an optical system for guiding the laser beam to an operation-applying portion of the cornea; means for cooling that portion of the cornea to undergo the operation; means for sprinkling or spraying a liquid medicine onto the cornea; and means for removing the liquid medicine supplied onto the cornea cooler of the cornea.

Although the present invention can be extensively applied to operations on the cornea of an eye employing an ultraviolet laser, the most preferred ultraviolet laser is an excimer laser.

In the present invention, before, during and after the operation, the operation-applying portion of the cornea of the eye is cooled to form a cooling barrier, thereby alleviating side effects due to heat produced by excimer laser radiation, and also suppressing the activity of the organism and cells of the cornea, thus suppressing an excessive reaction of the organism against excimer laser radiation. Also, the liquid medicine for remedy, protection, cure promotion and resolution purposes is suitably sprinkled or sprayed onto the operation-applying portion of the eye cornea, thereby protecting the eye cornea, accelerating the remedy, and preventing side effects such as opacity. The excess liquid medicine sprinkled on the cornea must be removed when the laser radiation is applied, and the irradiation of the laser beam is effected in an ON-OFF manner to produce pulses, and therefore the control is effected in such a manner that the sprinkling of the liquid medicine as well as the blowing-off of the liquid medicine by gas is carried out during a short time period (corresponding to the pulse interval) when the laser radiation is OFF. Instead of merely sprinkling the liquid medicine on the cornea, it can be sprayed in an atomized condition, in which case the effect is also achieved.

It is proper that the medicine for protecting the cornea and for alleviating the side effects contain, as ingredients, salts such as NaCl, $CaCl_2$, KCl and $MgCl_2$, buffer salts such as $NaH_2PO_4$ and $NaHCO_3$, and an energy source such as glucose and glutatione, and that the medicine be in the form of a solution having an osmotic pressure of 305~310 mOsm and PH 7.2~7.6.

According to results of animal tests, good results can be obtained when the cornea cooling temperature is 0°~10° C. In some cases, the operation may be conducted in a frozen condition of the cornea cooled to a temperature of not more than 0° C. In order to accurately control the cooling temperature to a desired value, it is necessary that a sensor for detecting the temperature of the cooling means should be provided, and that a temperature control means responsive to a signal from this sensor for controlling the temperature of the cooling means to a predetermined temperature should be provided. This temperature control can be effected quite simply and accurately by using Peltier elements as the cooling means.

BEST MODE FOR CARRYING OUT THE INVENTION

An eye cornea operation according to the present invention is initiated by starting the instillation of a liquid medicine on an eye and an internal administration of a medicine one week before the operation. This liquid medicine has the effect of alleviating troubles due to a photochemical thermal reaction involved in the operation using a laser, and more specifically has such effects as the safety of the cornea treatment, a promoted remedy after the operation and resolution, and it has been confirmed through animal tests that the liquid medicine is extremely effective when it contains as ingredients oxygltatione +salts+buffer salts+glucose+glutatione (tradename: BSS PLUS), RINDERON (steroid), TARIVID (antibiotic agent) and Sikon+Toki (burn curing medicine). RINDERON is made by SHIONOGI of Japan and its active ingredient is betamethasone sodium phosphate (available as follows: 0.4% and 2% in solution for injection; 0.01% in eye-dropping medicine; and 0.1% in liquid medicine for eye and ear). TARIVID is made by SANTEN of Japan and its active ingredient is ofloxacin (available as follows: 0.3% in eyedropping medicine and eye ointment). Sikon and Toki are available from DAIDO SEIYAKU CO., LTD. of Japan. By repeatedly instilling this liquid medicine on the eye before the operation, the concentration of the liquid medicine in the cornea is increased. It has been found that to internally administer an antiphlogistic, such as TATION and steroid or INDACINE, simultaneously with the instillation further enhances the effect. TATION is made by YAMANOUCHI of Japan and its active ingredient is glutathione (available as follows: 20% in powered form; 50 & 100 mg in tablet; 100, 200, 300, & 600 mg in eye injection; 100 mg in eye-dropping medicine). INDACINE is made by MANYU of Japan and its active ingredient is indometacin (available as follows: 25 mg in capsule).

Before starting the operation, the cooling of the cornea, as well as the sprinkling or spraying of a liquid medicine onto the cornea, is effected. Although the side effects are reduced only with the cooling, it has been confirmed through animal tests that the use of both the cooling and the liquid medicine further reduce the side effects. The liquid medicine is the same as that used for instillation. Sikon and Toki in this liquid medicine are herb medicines, and the Sikon serves to cure a burn, an inflammation and a tumefaction and also to lower a local temperature, while the TOKI serves to promote the effect of the Sikon.

Figure 1:
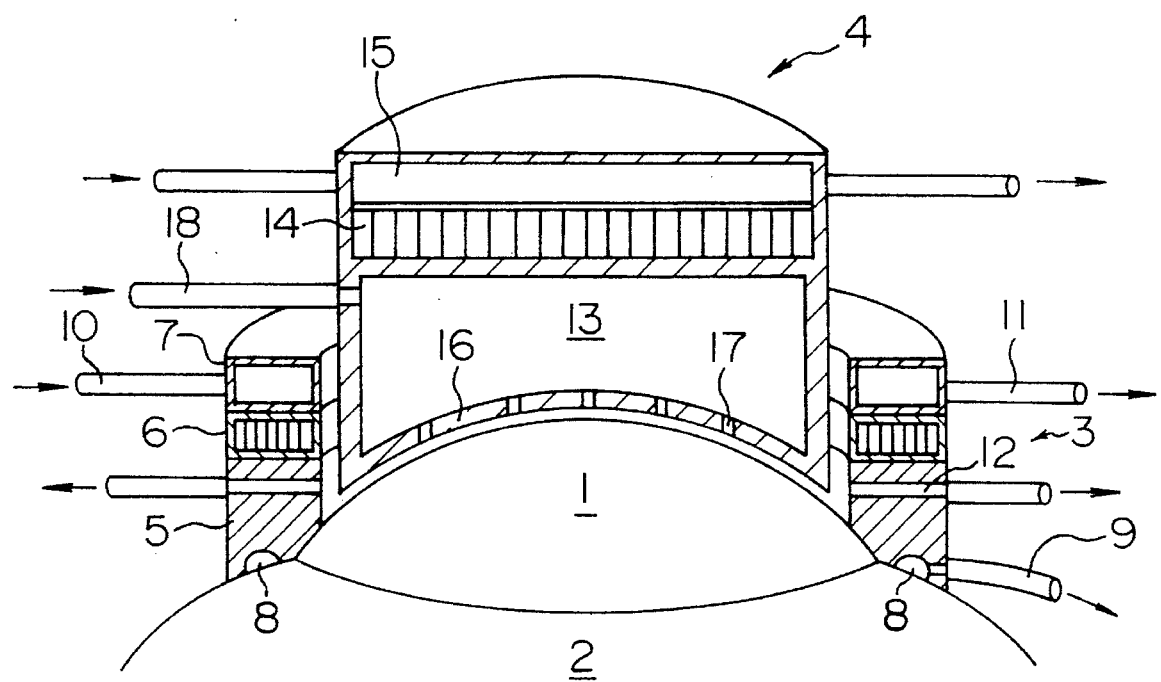
FIG. 1 is a cross-sectional view of one embodiment of a cornea cooling and liquid medicine supply apparatus used for an operation on the cornea of an eye by an ultraviolet laser.

FIG. 1 shows one embodiment of an apparatus for cooling the cornea as well as the sprinkling of the liquid medicine on the cornea. In FIG. 1, 1 denotes the cornea of an eye, and 2 denotes the sclera thereof. The cornea-cooling and liquid medicine-sprinkling apparatus comprises an outer tube 3 and an inner tube 4. The outer tube 3 comprises three-stage blocks 5, 6 and 7 integrally connected together, and is adapted to be placed on the sclera 2. A lower surface of the lower-stage block 5 is formed into a curved surface conforming in configuration to the surface of the sclera 2, and a downwardly-open annular suction chamber 8 is formed in this lower surface. The suction chamber 8 is connected to a vacuum source via a tube 9 so as to create a negative pressure therein, thereby holding the outer tube 3 on the sclera 2 by suction. During the operation, the eyeball is thus fixed in a stationary condition, and the optical axis of the eyeball is accurately positioned.

Peltier elements are incorporated in the intermediate-stage block 6, and is arranged with the heat-absorbing side directed toward the lower-stage block 5 while the heat-generating side is directed toward the upper-stage block 7. The upper-stage block 7 serves as a heatsink, and a cooling medium, flowed thereinto from a tube 10, cools the heat-generating side of the Peltier element in the block 6, and flows out into a tube 11. Thus, the temperature of the heat-absorbing side of the Peltier element is further lowered. The cooling temperature by the Peltier element can be controlled by electric current flowing through the Peltier element, and therefore there is provided an advantage that the cooling temperature can be easily controlled. Low-temperature gas such as cooled carbon dioxide gas, liquid nitrogen, liquid helium, Freon gas and the air, or a cooled liquid, or any arbitrary cooling liquid such as city water can be used as the cooling medium flowing through the heatsink 7.

The lower-stage block 5 is preferably made of metal such as platinum, gold, silver and stainless steel, but other material than metal such as ceramics can be used in so far as it has a high thermal conductivity. The lower-stage block 5 is cooled by the Peltier element in the intermediate-stage block 6, and cools the sclera 2 and the outer peripheral portion of the cornea 1, so that the peripheral portion of the cornea to undergo the operation is cooled from the periphery. Suction holes 12 are formed in the lower-stage block 5 for removing the liquid medicine, sprinkled on the cornea 1, before laser radiation as described later.

In the sequence from the bottom to the top, a liquid medicine reservoir portion 13, a Peltier element portion 14, and a heatsink 15 for cooling the Peltier element portion 14 are provided at the inner tube 4. A bottom wall 16 of the liquid medicine reservoir portion 13 is formed into a curved surface conforming in curvature to the surface of the cornea 1, and has a number of liquid medicine discharging holes 17. The liquid medicine reservoir portion 13 has a surrounding wall made of a thermally-conductive material similar to that of the lower-stage block 5 of the outer tube 3, and is cooled by the Peltier element 14 above it, so that the liquid medicine therein is cooled, and also the bottom wall 16 is cooled, thereby cooling the cornea 1 disposed in contact with the bottom wall 16. 18 denotes a tube for supplying the liquid medicine to the liquid medicine reservoir portion 13. Incidentally, it is desirable that a cooling device utilizing Peltier elements be provided midway on the tube 18 so as to beforehand cool the liquid medicine to be supplied to the liquid medicine reservoir portion 13.

When the above apparatus is used for providing a pretreatment for the operation, the outer tube 3 is always kept fixed on the sclera 2 while the inner tube 4 is moved upward and downward between a position where the inner tube 4 is in contact with the cornea 1 and a position where the inner tube is upwardly apart slightly from the cornea 1, thereby effecting the cooling of the cornea 1 and the supply of the liquid medicine onto the cornea 1 alternately. After this treatment, the liquid medicine on the cornea 1 is finally removed by suction through the suction holes 12 formed in the outer tube 3.

Figure 2:
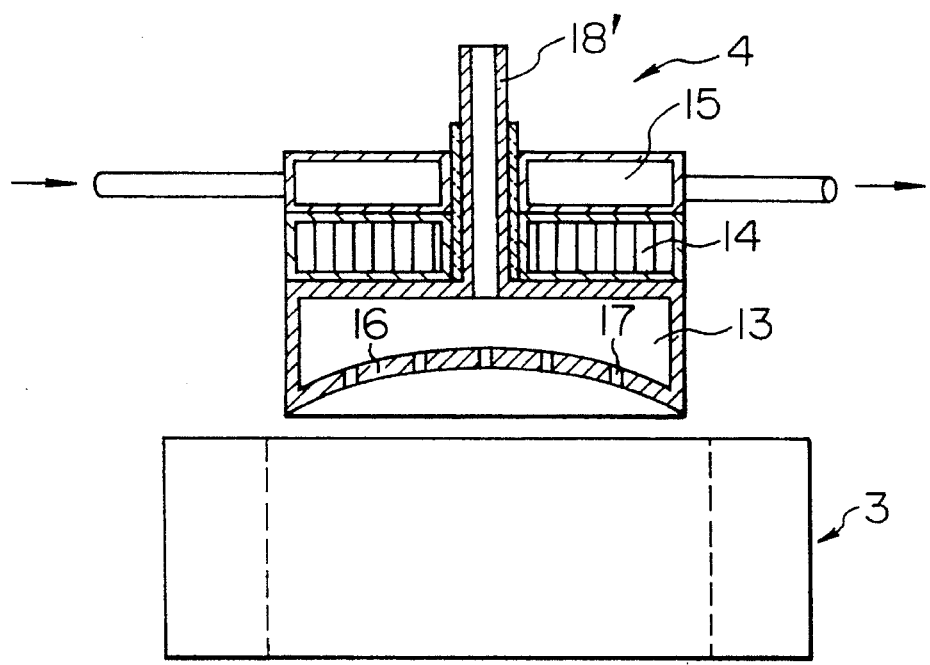
FIG. 2 is a cross-sectional view of an embodiment obtained by modifying part of the apparatus of FIG. 1.

FIG. 2 shows a modification of the apparatus of FIG. 1 which differs from the embodiment of FIG. 1 only in that a tube 18' for supplying the liquid medicine to the liquid medicine reservoir portion 13 passes through a central portion of the inner tube 4, and extends upwardly. The inner tube 4 can be withdrawn from the outer tube 3 as in the embodiment of FIG. 1.

Figure 3:
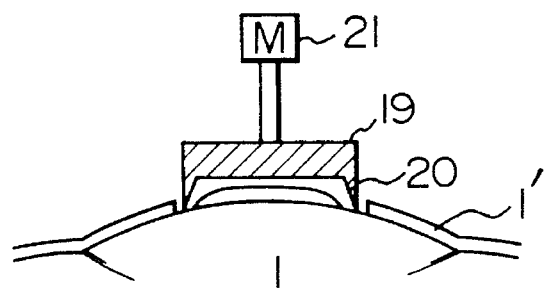
FIG. 3 is a front cross-sectional view of one embodiment of a corneal epithelium separating device.

The cooling of the cornea and the sprinkling of the liquid medicine on the cornea are carried out as described above before the operation, and thereafter the epithelium of the cornea is separated. The following devices can be used for separating the epithelium. FIG. 3 shows one example of a separation device in which an annular blade 20, projecting from a lower surface of a disk 19 at a peripheral edge portion thereof, is rotated by a motor 21, and the blade 20 is engaged with that portion of the epithelium 1' covering the surface of that portion of the cornea (stroma) 1 to undergo the operation, and is rotated to form a circular line of cut having a depth of 30–40μ. The height of the blade projected from the lower surface of the disk 19 is set to 30–40μ so that it will not damage the cornea stroma, and the lower surface of the disk 19 serves as a stopper so that the line of cut in the epithelium will not be deepened further. Without using the motor, the disk may be pressed against the cornea form the upper side with the hand, and is rotated, thereby forming a line of cut. The annular blade has a diameter of 4.5–10 mm. A piece of the epithelium formed by the line of cut is removed by a spatula.

Figure 4A:
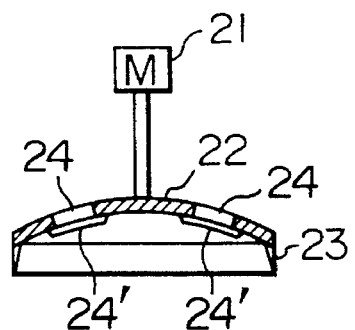
FIG. 4a and FIG. 4b are a front cross-sectional view and a bottom view of another embodiment of a corneal epithelium separating device, respectively.
Figure 4B:
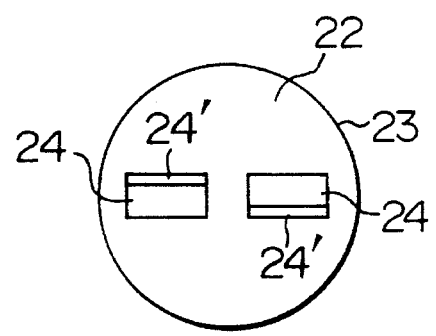

FIGS. 4a and 4b are a cross-sectional view and a bottom view of another example of an epithelium separation device, respectively. A disk 22 rotated by a motor 21 is curved downwardly into agreement with the curvature of the cornea, and an annular blade 23 is projected from a lower surface of this disk at a peripheral edge portion thereof. Slits 24 are formed in the disk 22, and a blade 24' is formed along one edge of each slit 24. In this embodiment, a circular line of cut is formed in the epithelium of the cornea by the blade 23, and that portion of the epithelium disposed inside this line of cut is removed by the blades 24', and is discharged through the slits 24. The above separating operation is carried out in the apparatus of FIG. 1 or FIG. 2 while continuing the cooling of the cornea, with the outer tube 3 fixed to the sclera 2 but with the inner tube 4 removed.

After the epithelium of the cornea is separated, the inner tube 4 is again fitted in the outer tube 3 in the apparatus of FIG. 1 or FIG. 2, and the cooling of the cornea and the sprinkling of the liquid medicine are effected.

Figure 5:
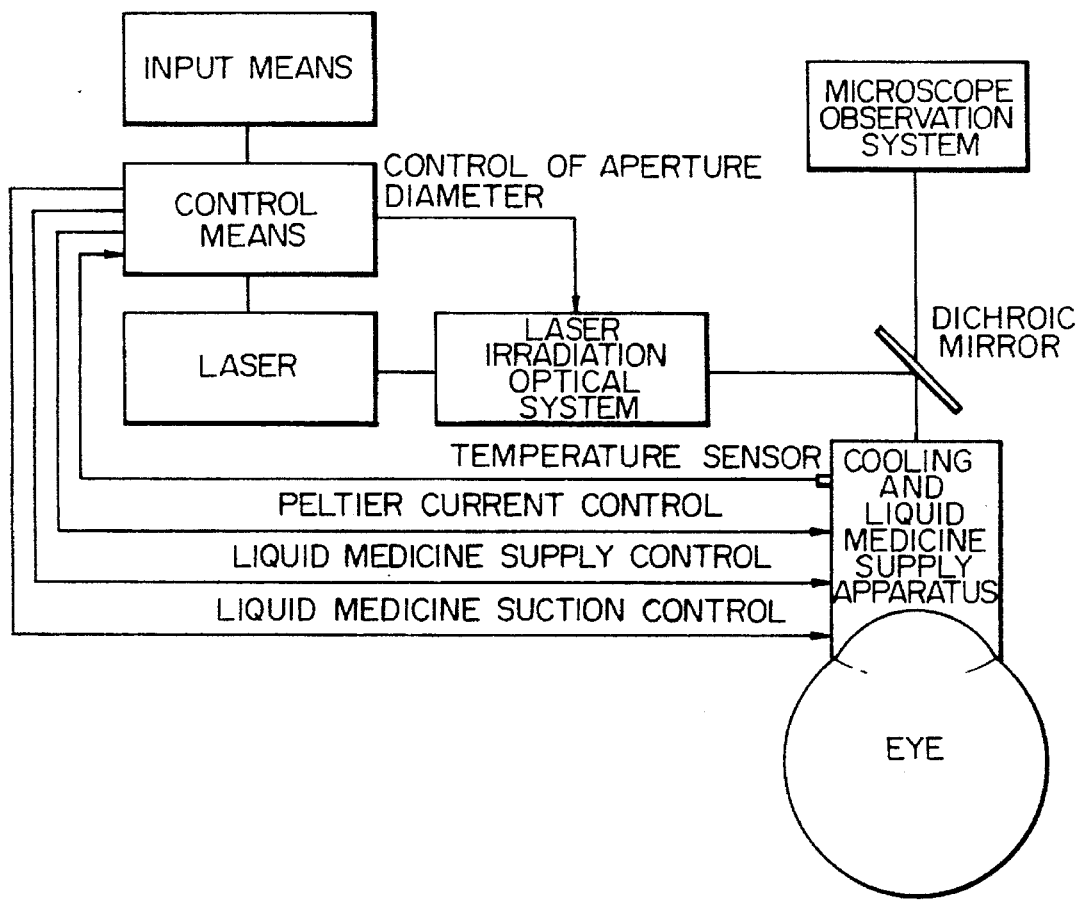
FIG. 5 is a block diagram showing a control system for the apparatus for conducting a corneal operation according to the present invention.

Then, a corneal ablation operation is carried out by excimer laser radiation. FIG. 5 is a block diagram showing a general construction of an excimer laser control system. By controlling a diaphragm aperture in accordance with an abnormal refraction condition, a laser beam is adjusted in energy distribution, and is reflected by a dichroic mirror, and is applied to that portion of the cornea to undergo the operation. The laser beam-applied portion of the cornea to undergo the operation is observed by a microscope through the dichroic mirror. Where the Peltier elements are used as means for cooling the cornea, the temperature of the heat-absorbing portion of the Peltier element is detected by a temperature sensor, and electric current flowing through the Peltier element is subjected to a feedback control so that this temperature can be brought into a predetermined temperature.

Figure 6:
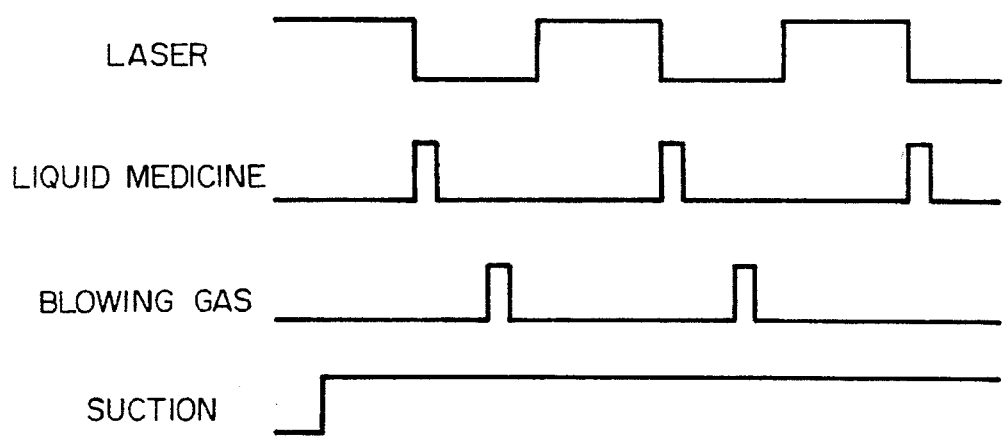
FIG. 6 is an explanatory diagram showing the timings of the operations used in the operation according to the present invention.
Figure 7:
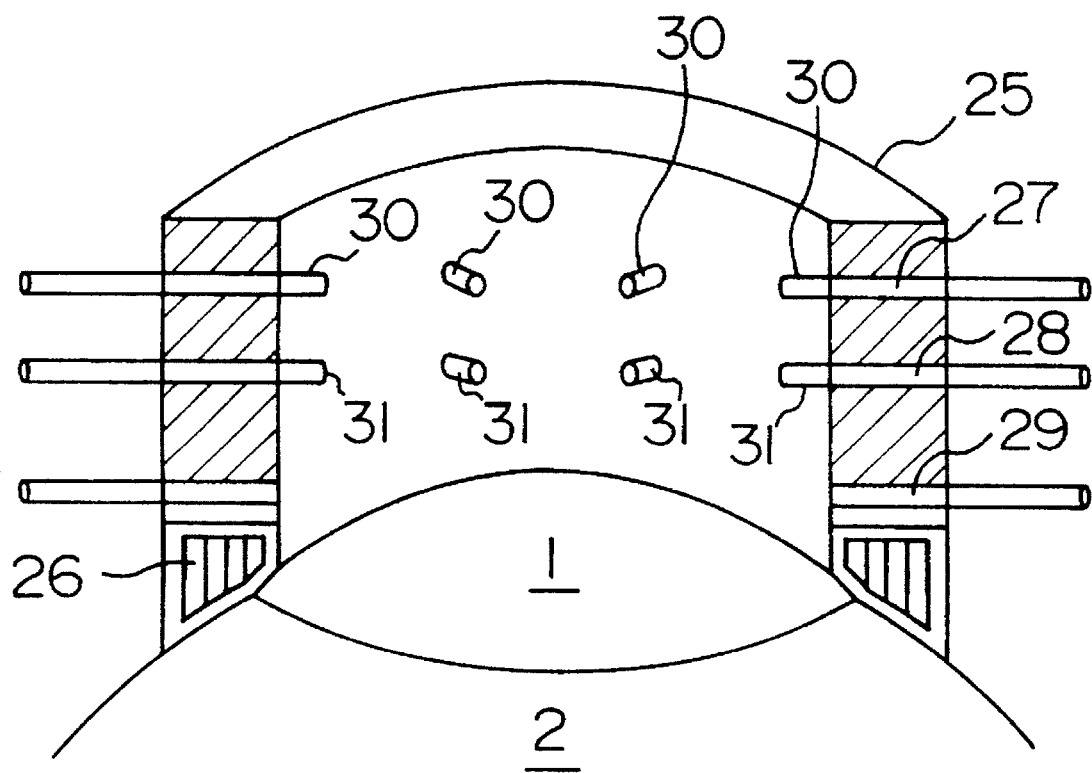
FIG. 7 is a perspective view showing the cross-section of a half of an embodiment of an apparatus for effecting the cooling of the cornea and the spraying of a liquid medicine during the operation where the cornea is deeply cut.

The laser beam is emitted as pulses as shown in FIG. 6, and is intermittently applied onto the cornea. During laser radiation, the liquid medicine should not be deposited on the cornea, and therefore the laser radiation, the supply of the liquid medicine and the blowing of gas are controlled at such timings that the liquid medicine is supplied immediately after the laser radiation is off, and is removed from the cornea, for example, by gas blown thereto immediately before the laser radiation is on, and is discharged through the suction holes always maintained under negative pressure.

Where the operation is to be conducted by a scanning method, with a spot of the excimer laser made small, and where the side effects are small as in an operation for myopia, astigmatism or hyperopia of a slight degree, there can be used a method in which the inner tube 4 is removed with the outer tube 3 kept fixed in the apparatus of FIG. 1 or FIG. 2, and only the peripheral portion of the cornea to undergo the operation continues to be cooled, and the excimer laser radiation is applied through the central portion of the outer tube 3 to that portion of the cornea to undergo the operation, without cooling the central portion of the cornea and without supplying the liquid medicine to the cornea.

Where the diameter of the spot of excimer laser radiation is large enough to produce large energy, and where the ablation of the cornea is deep because of an operation for abnormal refraction of a high degree, the cooling of the cornea, as well as the supply of the cooled remedy liquid medicine to the cornea, must be effected even during the operation by the excimer laser. FIG. 7 shows one example of apparatus used in such a case. Instead of the apparatus of FIG. 1 or FIG. 2, the apparatus of FIG. 7 is placed on the sclera 2 after the separation of the corneal epithelium is effected. The apparatus of FIG. 7 comprises a cylindrical member 25 having generally the same size as that of the outer tube 3 of the apparatus of FIG. 1 or FIG. 2, and its lower end portion, adapted to contact the sclera 2 and a peripheral portion of the cornea 1, is constituted by an assembly of Peltier elements 26. Although not shown, an eye fixing means such as a suction chamber as in the outer tube of FIG. 1 or claws, is provided on that surface of the Peltier elements adapted to contact the sclera 2. Remedy liquid medicine supply passageways 27, pressurized gas supply passageways 28 and liquid medicine suction holes 29 are formed through a cylindrical wall above the Peltier elements in this order from the upper side. A liquid medicine spray nozzle 30 is mounted on an inner end of the passageway 27, and a pressurized gas injection nozzle 31 is mounted on an inner end of the passageway 28. An excimer laser beam is applied from the upper side of the cylindrical member 25 to the cornea 1 through a generally central portion thereof.

During the operation, the Peltier elements 26 cool the sclera 2 around the cornea 1 undergoing the operation, as well as the peripheral portion of the cornea, and the excimer laser is irradiated as pulses as shown in FIG. 6. During the interruption of the laser radiation, the remedy liquid medicine is sprayed from the liquid medicine spray nozzles 31 onto the cornea 1 at a predetermined timing, and pressurized gas is injected from the injection nozzles 31 at a predetermined timing to blow off the liquid medicine deposited on the cornea 1, and this liquid medicine is removed by suction through the suction holes 29. Thus, with the apparatus of FIG. 7, not only the cooling of the cornea but also the supply of the remedy liquid medicine are effected even during the operation by the excimer laser, and therefore even if a deep ablation of the cornea 1 is effected using large energy, the production of side effects can be kept to a low level. Particularly in this apparatus, if the supply of the liquid medicine to the cornea is effected not only by sprinkling but also by spraying, this further enhances the effect.

After the operation, the cooling of the cornea and the supply of the liquid medicine are sufficiently effected using the apparatus of FIG. 1 or FIG. 2. It is appropriate that the cooling temperature be 4° C., but if the cooling is effected too long, the function of the endothelial cells of the cornea is lowered, so that the cornea is subjected to swelling. Therefore, the cooling by the Peltier elements is stopped in a suitable period of time, and thereafter only the supply of the cooled remedy liquid medicine is effected. Time required for this is 2~3 minutes.

Then, an ointment of steroid, such as for example a ointment prepared by mixing, with NEO-MEDROL EE ointment, an antibiotic agent such as TARIVID, INDACINE (non-steroid antiphlogistic), BSS PLUS or TATION, Sikon plus Toki, and neurotensin and fibronectin plus EGF (Epidermal Growth Factor), is applied to the eye, and an eye bandage is used. NEO-MEDROL EE ointment is made by SUMITOMO, NIHON UPJOHN of Japan and its active ingredient is fradiomycin sulfate and methylprednisolone (available as follows: 1 g ointment containing 1 mg of methylprednisolone and 3.5 mg of fradiomycin sulfate). Alternatively, a disposable soft lens (for example, the tradename "ACUVUE") or a collagen shield impregnated with a liquid medicine composed of these ingredients is put into the eye to cover the cornea. By doing so, the wound is quickly curred and the pain after the operation is eased. Also, an injection of steroid, an antibiotic agent and Sikon is applied under the conjunctiva.

Figure 8:
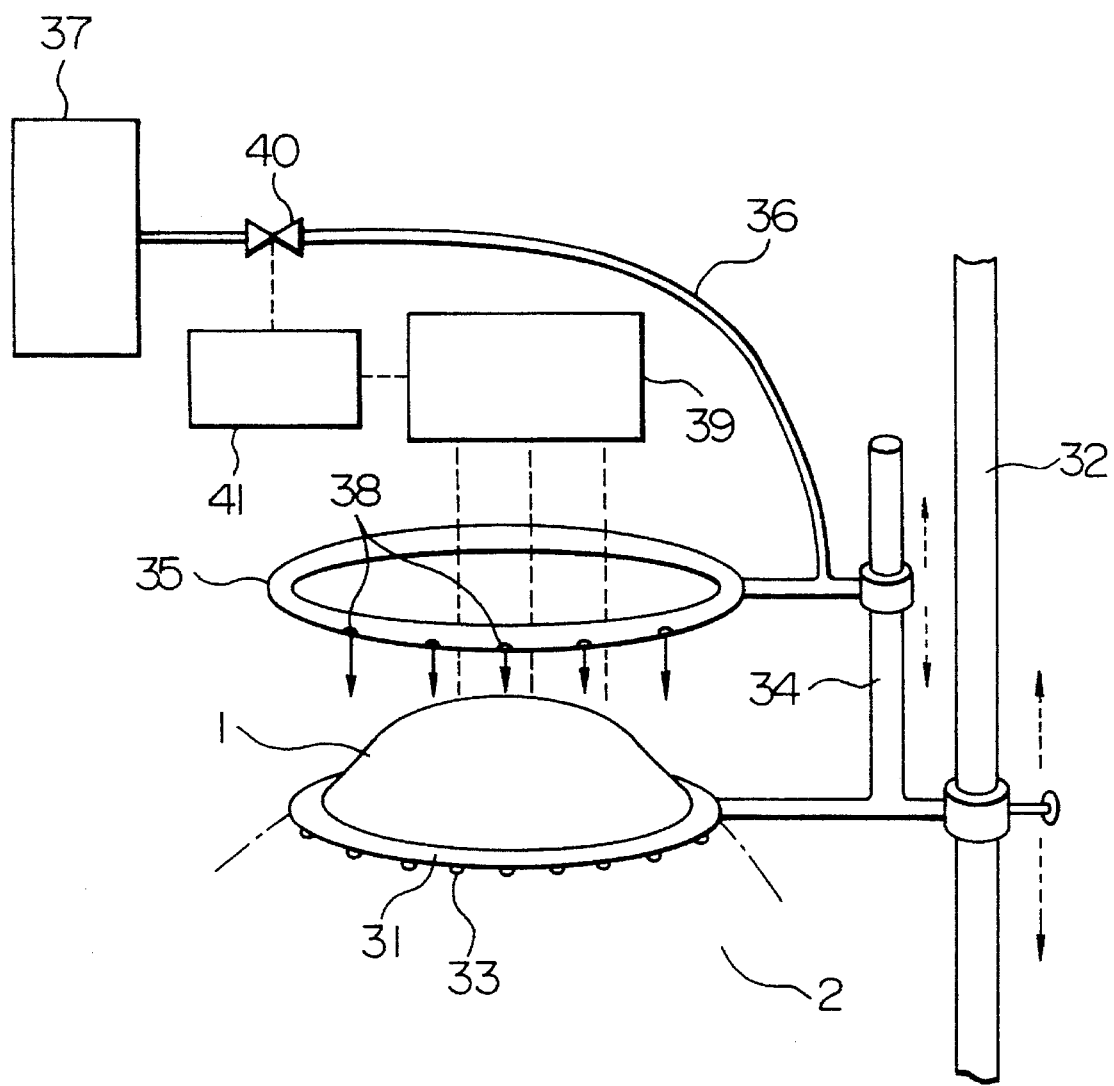
FIG. 8 is a perspective view of an embodiment of an apparatus used for a slight-degree eye cornea operation.

Various other embodiments of apparatus used for an eye cornea operation of the present invention will now be described. FIG. 8 shows an apparatus for conducting a slight-degree eye cornea operation. An eye fixing ring 31 is mounted on a support post 32 for upward and downward movement, and is placed in such a manner as to be slightly pressed against the sclera 2 around the cornea 1 in surrounding relation to the cornea. A number of claws 33 are mounted on a lower surface of the fixing ring 31, and fix the eye against movement relative to the fixing ring 31, thereby properly positioning the optical axis of the eye.

A ring-shaped cooling pipe 35 is fixedly provided above the fixing ring 31 through a support bar 34. The cooling pipe 35 is connected to a cooling gas bomb 37 via a connecting pipe 36, and cooling gas is injected toward the cornea 1 from a number of injection nozzles 38 provided in a lower surface of this cooling pipe to cool the cornea 1. Carbon dioxide gas, liquid nitrogen, liquid helium or the like is used as the cooling gas. Instead of the cooling gas, a cooling liquid such as cooled BSS PLUS, physiological saline and a Ringer's solution may be used. The cooling pipe 35 is fixed to the support bar 34 in such a manner that the distance between this cooling pipe and the cornea 1, as well as the angle of this cooling pipe relative to the cornea 1, can be adjusted, and the cooling pipe beforehand forms a cooling barrier around the portion to undergo the operation.

An excimer laser 39 is mounted above the cooling pipe 35, and applies laser beams to the cornea 1 through a space encircled by the cooling pipe 35. Before and after the irradiation of the laser beam, a liquid medicine, having such effects as cornea remedy, cure promotion and resolution, is sprinkled on the cornea by the use of a suitable device. It is also necessary to blow off this liquid medicine from the cornea before the irradiation.

A shut-off valve 40 is provided on the connecting pipe 36 connecting the cooling pipe 35 to the cooling gas bomb 37, and the opening and closing operation of this shut-off valve 40 is associated with the operation of the excimer laser 39 by a controller 41. When the laser beam is to be applied, the shut-off valve 40 is closed to interrupt the blowing of the cooling gas, and when the irradiation of the laser beam is stopped, the cooling gas is blown. Thus, the blowing of the cooling gas and the irradiation of the laser beam can be sequentially repeated. Alternatively, the treatment by the excimer laser may be carried out while continuously blowing the gas.

The thickness of the fixing ring 31 is set to 1~5 mm, and its diameter is set to 12~30 mm. The thickness of the cooling pipe 35 is set to 2~15 mm, and the inner diameter of the gas passageway is set to 1~13 mm, and its pipe diameter is set to 6~50 mm.

Figure 9:
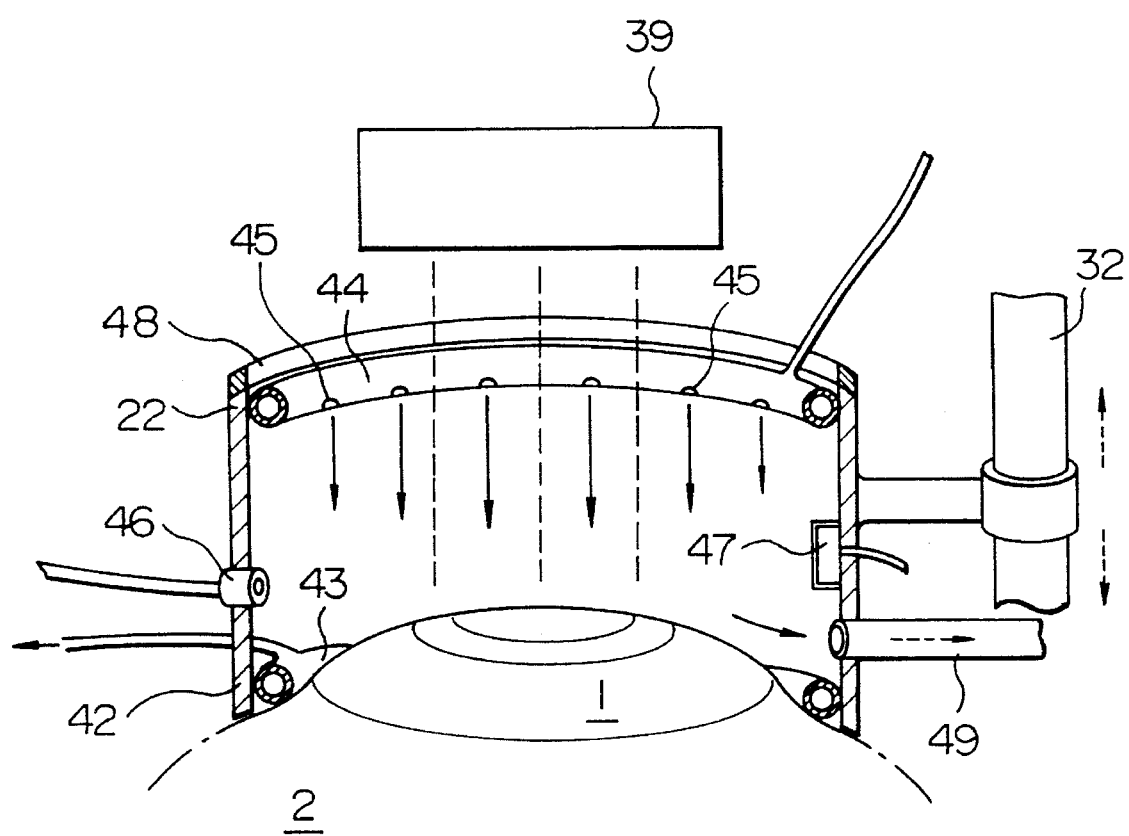
FIG. 9 is a perspective view showing the cross-section of a half of an embodiment of an apparatus used for a medium- and high-degree eye cornea operation, showing an internal structure thereof.

FIG. 9 shows an apparatus for conducting a medium-degree eye cornea operation, and a hollow cylindrical fixing tube 42 made, for example, of an acrylic material, is mounted on a support post 32 for upward and downward movement. The fixing tube 42 has such a diameter that it covers the cornea 1 of the eye and part of the sclera 2 around the cornea. A suction tube 43, which communicates with a vacuum pump (not shown) and has a number of spaced narrow holes for contact with the sclera 2, is provided along the bore of the fixing tube 42 at a lower end portion thereof, and the fixing tube 42 is fixed to the eye by suction.

A cooling pipe 44, having a number of downwardly-directed nozzles 45 formed therein, is mounted along the inner surface of the fixing tube 42 at an upper end portion thereof, and cooling gas or a cooling liquid is applied toward the eye cornea to form a cooling barrier at the operation-applying portion of the cornea.

An excimer laser 39 is mounted above the fixing tube 42, and applies laser beams to the cooled cornea through a hollow portion of the fixing tube 42. Before and after the irradiation of the laser beam, a liquid medicine is sprinkled or sprayed onto the cornea by the use of a suitable device as described above, and it is also necessary to blow off this liquid medicine from the cornea before the irradiation.

Further, a microcamera 46 connected to a television monitor (not shown) is mounted on the fixing tube 42, so that the condition of the operation on the cornea can be monitored through the television monitor, and also a temperature sensor 47 is provided so that the operation can be conducted while confirming the cooling condition of that portion of the cornea undergoing the operation, as well as the condition of formation of the cooling barrier. This is useful. The timing of irradiation of the laser beam, as well as the timing of blowing of the cooling gas, may be controlled by the use of a controller, as in the apparatus of FIG. 8.

Referring to the type of apparatus for conducting a high-degree eye cornea operation, the upper open end of the fixing tube 42 in the apparatus of FIG. 9 is closed by a lid 48 made of a material having laser beam-transmitting properties, such as quartz glass. When the fixing tube 42 with this lid 48 is fixed by suction on the eye, the interior of the fixing tube 42 is sealed from the outside air, and therefore the cooling gas injected from the cooling pipe 44 will not leak to the exterior, so that the cooling of the cornea can be carried out in a short time period. By connecting a suction pipe 49 to the fixing tube 42, the interior of the fixing tube 42 can be evacuated by a vacuum pump (not shown), so that the cornea cut by the laser beam from the excimer laser can be discharged to the exterior. By evacuating the interior of the fixing tube 42 through this suction pipe 42, the effect of bonding of the fixing tube relative to the eye can be further enhanced. Moreover, the use of the fixing tube 42 can prevent side effects caused by leakage of reflection light and scattered light of the excimer laser to the exterior.

Figure 10:
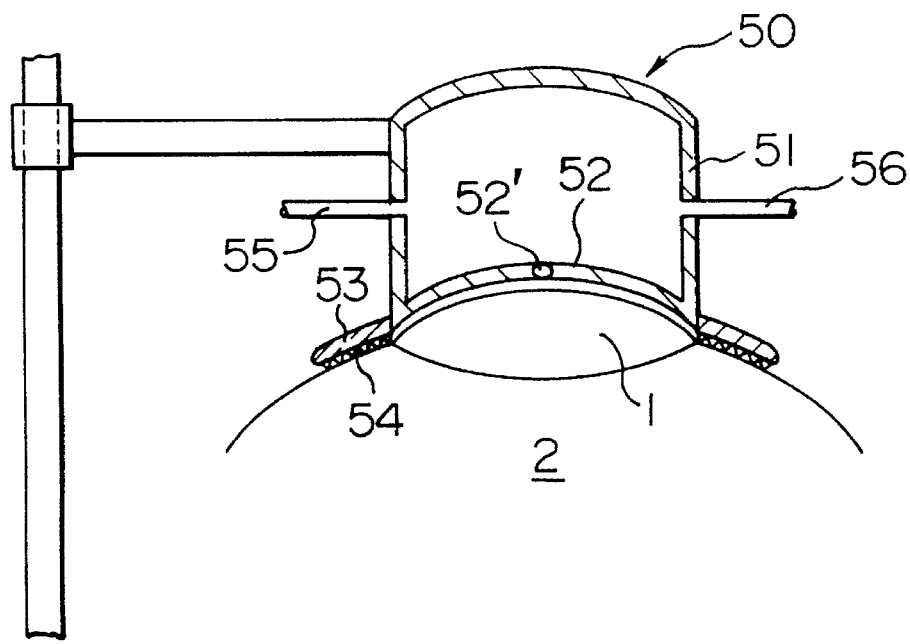
FIG. 10 is a cross-sectional view of an embodiment of an apparatus for cooling the cornea before and after an eye cornea operation, in which a cooling medium is used as cooling means.

FIG. 10 shows an embodiment of apparatus for only cooling the cornea before and after an eye cornea operation. A hollow cooling member 50 includes a cylindrical side wall 51, and a bottom wall 52 having a concave surface conforming in curvature to the cornea 1 of an eye. This member is preferably constructed of metal such as platinum, gold, silver and stainless steel, but may be constructed of other material than metal such as ceramics as long as it has a high thermal conductivity. In some cases, the cooling member 50 can be formed into a flexible construction by a flexible metallic film, silicone film, synthetic rubber film or any one of various kinds of plastic films, in which case the degree of contact of the bottom wall 52 with the cornea 1 is enhanced, which is desirable. The height of the cooling member 50 is 10 mm, and its diameter is 10~30 mm.

A flange 53 is formed on and projected outwardly from the outer periphery of the cooling member 50 at the lower end thereof in continuous relation to the bottom wall 52, and claws 54 for engaging the sclera 2 to fix the eye relative to the cooling member 50 are formed on a lower surface of this flange. A cooling medium feed pipe 55 and a cooling medium discharge pipe 56 are connected at their one ends to the side wall 51 of the cooling member 50, and the other ends of these pipes are connected to a cooling medium reservoir (not shown). Thus, a cooling medium, such as low-temperature gas and low-temperature liquid, flows through the cooling member 50 to cool the cornea 1. Preferably, the outer diameter of the cooling medium feed and discharge pipes 55 and 56 is 2~15 mm, and their inner diameter is 1~13 mm.

Further, a temperature sensor 52' such as a thermistor may be provided in the bottom wall 52 of the cooling member 50 for accurately controlling the temperature of the cornea to a set temperature, and if necessary, supply pipes and suction pipes for physiological saline, BSS PLUS, a Ringer's solution, an anesthetic liquid and etc., a microcamera connected to a television monitor, and so on may be provided in the vicinity of the cooling member 50. As the cooling medium, cooling gas, such as carbon dioxide, liquid nitrogen, liquid helium, Freon gas and the air can be used, and also a cooling liquid such as cooled city water can be used. During the operation by the excimer laser, this cooling member must be removed and replaced by other cooling device capable of allowing the irradiation of the excimer laser.

Figure 11:
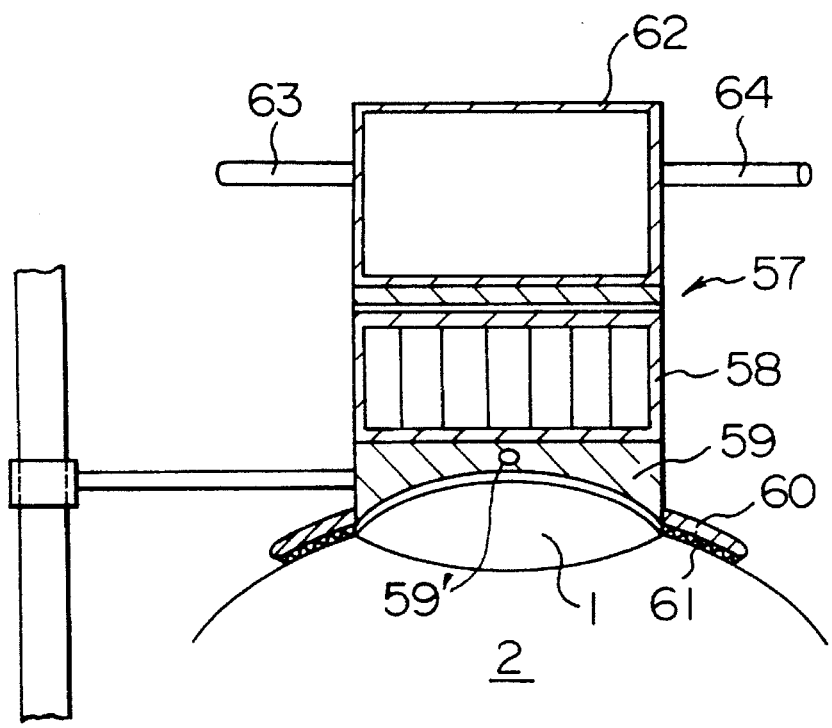
FIG. 11 is a cross-sectional view of an embodiment of an apparatus for cooling the cornea before and after an eye cornea operation, in which a Peltier element is used as cooling means.

FIG. 11 shows another embodiment of apparatus for only cooling the cornea before and after an eye cornea operation, as in FIG. 10. This embodiment has a feature that a cooling member 57 is cooled by a Peltier element 58. A support block 59 of metal with good thermal conductivity is mounted under the Peltier element 58, and a lower surface of the support block 59 is formed into a concave surface conforming in curvature to the cornea 1, and when in use, this lower surface is in contact with the surface of the cornea 1 to cool the cornea. 59' denotes a temperature sensor provided in the support block. A flange 60 is formed on and projected outwardly from the periphery of the support block 59 at a lower end thereof, and claws 61 for engaging the sclera portion around the cornea of the eye are formed on a lower surface of this flange to fix the eye in a stationary condition.

A heatsink 62 is provided in contact with an upper portion of the Peltier element 58, that is, a heat-generating portion of the Peltier element. A cooling medium flows through the heatsink 62 via a cooling medium feed pipe 63 and a cooling medium discharge pipe 64. The function of the heatsink 62 is to cool the heat-generating portion of the Peltier element 58 to relatively lower the temperature of a heat absorbing portion of the Peltier element 58 disposed in contact with the support block 59. As in the apparatus of FIG. 10, if necessary, a temperature sensor, supply pipes and suction pipes for physiological saline, BSS PLUS, a Ringer's solution, an anesthetic liquid and etc., a microcamera connected to a television monitor, and so on may be provided in the vicinity of the cooling member 57.

The apparatus of FIG. 11 employs the Peltier element, and therefore a lightweight and compact construction is achieved; since the configuration of the element can be freely chosen, this is best suited for the cooling of the eye cornea; by controlling electric current, a more precise temperature control is possible, and a temperature response is good; since there is used no moving mechanism, vibrations and noises are not produced; since no mechanical part is used, the durability is good, and a stable performance can be achieved for a long period of time; and since there is little leakage of the cooling medium, the safety and sanitariness are achieved. Thus, these and other effects can be obtained.

Figure 12:
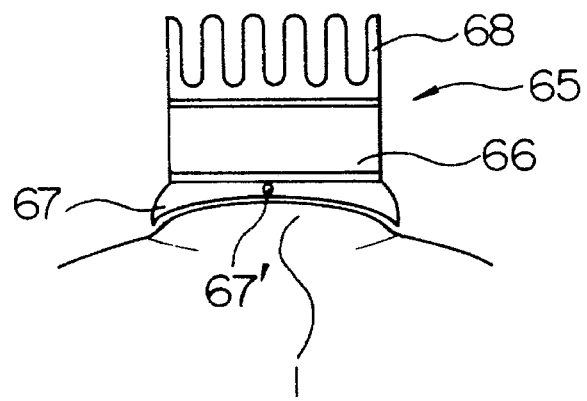
FIG. 12 is a cross-sectional view of another embodiment of an apparatus for cooling the cornea before and after an eye cornea operation, in which a Peltier element is used as cooling means.

FIG. 12 shows a further embodiment of cooling member utilizing Peltier elements. The cooling member 65 includes a support block 67, which is mounted under the Peltier elements 66, and has a lower surface conforming in configuration to the surface of the cornea 1. Instead of a heatsink, cooling fins 68 are provided on the Peltier elements 66 to radiate heat of a heat-generating portion of the Peltier element 66. 67' denotes a temperature sensor mounted in the support block 67.

Figure 13:
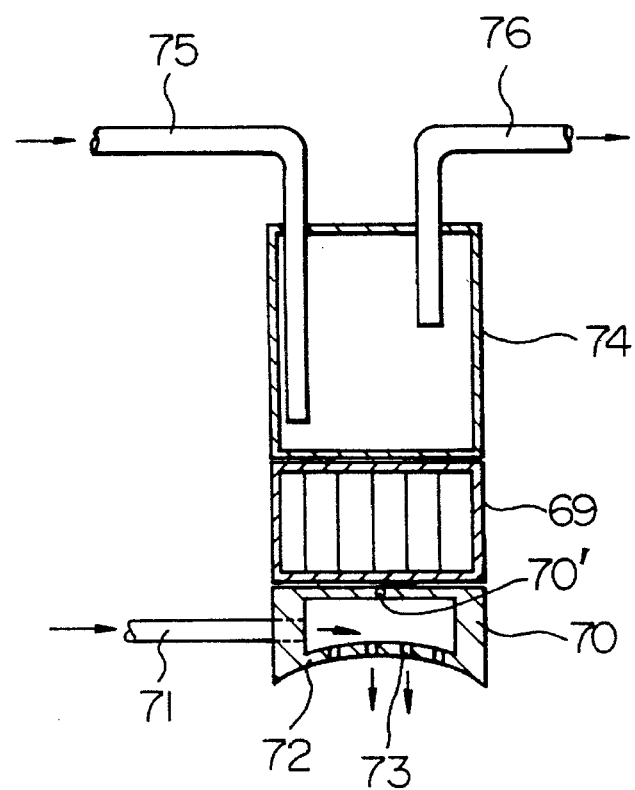
FIG. 13 is a cross-sectional view of an embodiment of an apparatus for cooling the cornea and the sprinkling of a liquid medicine before and after an eye cornea operation.

FIG. 13 shows an apparatus capable of effecting the cooling of the cornea and the supply of the remedy liquid medicine before and after the operation. A hollow cooling block 70 is mounted under Peltier elements 69, and the liquid medicine is supplied to the interior of the block 70 via a liquid medicine supply pipe 71. A lower surface of the cooling block 70 has a configuration conforming to the surface of the cornea, and a number of liquid medicine discharge ports are formed through a bottom wall 72 thereof. The cooling block 70 is made of a thermally-conductive material, and is cooled in contact with a heat-absorbing portion of the Peltier elements 69. A heatsink 74 is provided in contact with an upper or heat-generating portion of the Peltier elements 69, and a cooling medium flows through the heatsink 74 via a cooling medium feed pipe 75 and a cooling medium discharge pipe 76 to cool the heat-generating portion of the Peltier element 69. The above apparatus can not be used during the operation by the excimer laser. The liquid medicine to be supplied to the cooling block 70 may be pre-cooled by Peltier elements (not shown) during the passage of this liquid medicine through the pipe 71 so that the cooling effect can be further enhanced. In this embodiment, a temperature sensor 70' is mounted in an upper wall of the cooling block 70 because of the arrangement of wiring.

Figure 14:
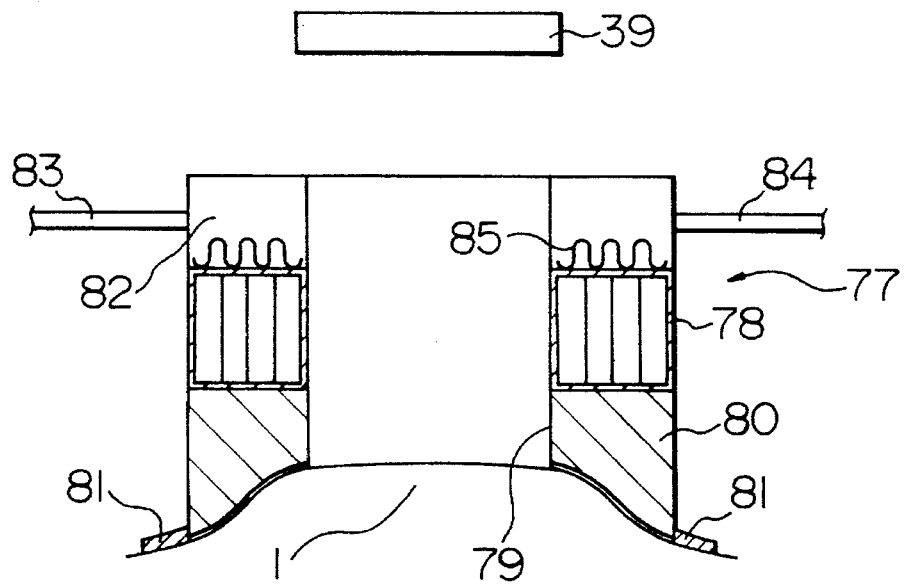
FIG. 14 is a cross-sectional view of an embodiment of an apparatus for cooling the cornea during an eye cornea operation.
Figure 15:
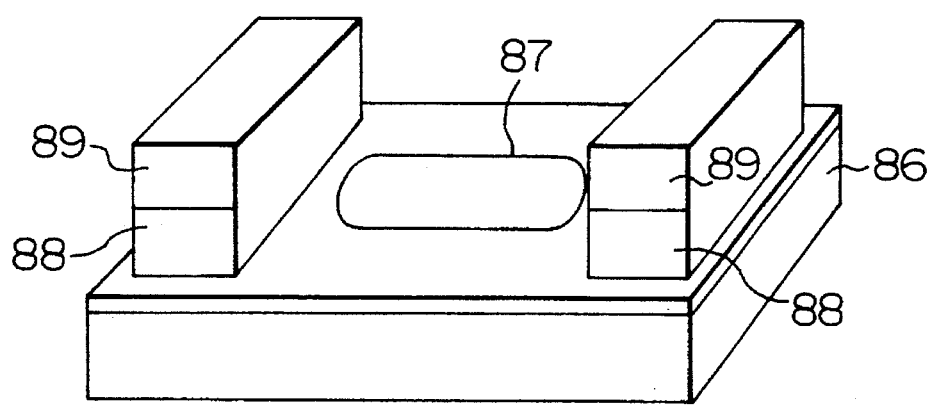
FIG. 15 is a cross-sectional view of another embodiment of an apparatus for cooling the cornea during an eye cornea operation.

FIG. 14, FIG. 15 and FIG. 16 respectively show apparatuses that employ Peltier elements, and are capable of cooling the cornea even during the operation. FIG. 14 shows a cooling member 77 of a cylindrical shape which has a thick wall, and has at its central portion a circular bore capable of passing a laser beam therethrough. A cooling block 80 of a thermally-conductive material having a circular central bore 79 is mounted under Peltier elements 79 arranged in an annular manner, and a lower surface of this cooling block has a configuration conforming to the surface of the cornea 1. 81 denotes a flange that has at its lower surface a fixing means, such as claws and suction tubes, for engaging the sclera. An annular heatsink 82, to which a cooling medium feed pipe 83 and a cooling medium discharge pipe 84 are connected, is mounted on the Peltier elements 78. Fins 85 mounted on a heat-generating portion of the Peltier elements 78 project into the heatsink 82, and are cooled by a cooling medium flowing through the heatsink 82. By cooling the fins 85, the heat-generating portion of the Peltier elements 78 is cooled, so that the temperature of a heat-absorbing portion of the Peltier elements 78 is relatively lowered, thereby enhancing the effect of cooling of the cornea by the cooling block 80. 39 denotes an excimer laser provided above the central portion of the cooling member 77, and a laser beam can reach the cornea through the central bore of the cooling member 77.

FIG. 15 show a cornea cooling apparatus in which a bore 87 is formed through a central portion of a rectangular cooling block 86 of a thermally-conductive material, and a recess, having a curved surface conforming in configuration to the cornea, is formed in a central portion of a lower surface of the cooling block 86. Two rectangular Peltier elements 88 are mounted respectively on right and left side portions of an upper surface of the cooling block 86 in opposed relation to each other, and a heatsink 89 having the same shape as that of the Peltier element is mounted on each of the Peltier elements 88. The cooling operation of this apparatus will be clear from the description of the above various apparatuses. A laser beam is applied to the cornea through the bore 87. This apparatus has an advantage that commercially-available Peltier elements can be used. The long sides of the cooling block may be formed into an arcuate configuration so that it can be easily put in the eye.

Figure 16A:
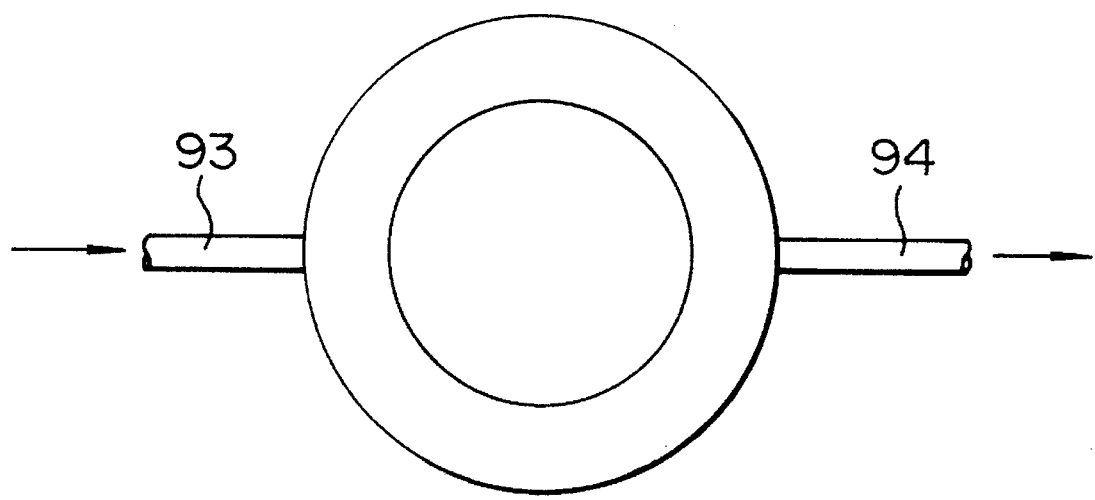
FIG. 16a and FIG. 16b are a plan view and a cross-sectional view, respectively, of a further embodiment of an apparatus for cooling the cornea during an eye cornea operation in which a Peltier element is used as cooling means.
Figure 16B:
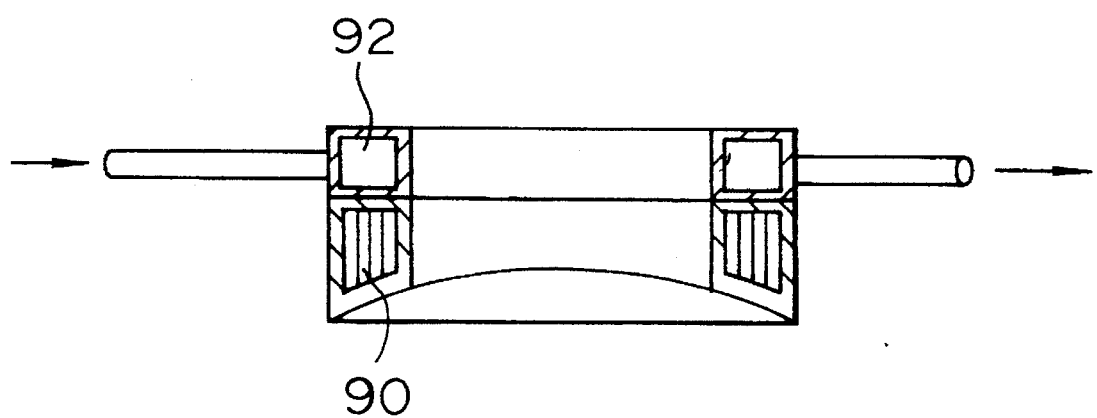

In the apparatus of FIGS. 16a and 16b, a Peltier element 90 is arranged in a circular manner with a bore formed at its central portion, so that the Peltier element itself serves as a cooling block. A heatsink 92, which has a central bore 91, and has the same configuration as that of the Peltier element, is mounted on the Peltier element. 93 and 94 denote a cooling medium feed pipe and a cooling medium discharge pipe, respectively, which are connected to the heatsink 92. A laser beam is applied to the cornea through the bore 91. The cornea cooling effect is the same as in the apparatus of FIG. 15. In this embodiment, the cooling block may be modified into a rectangular shape so that the Peltier element can be easily manufactured.

Figure 17:
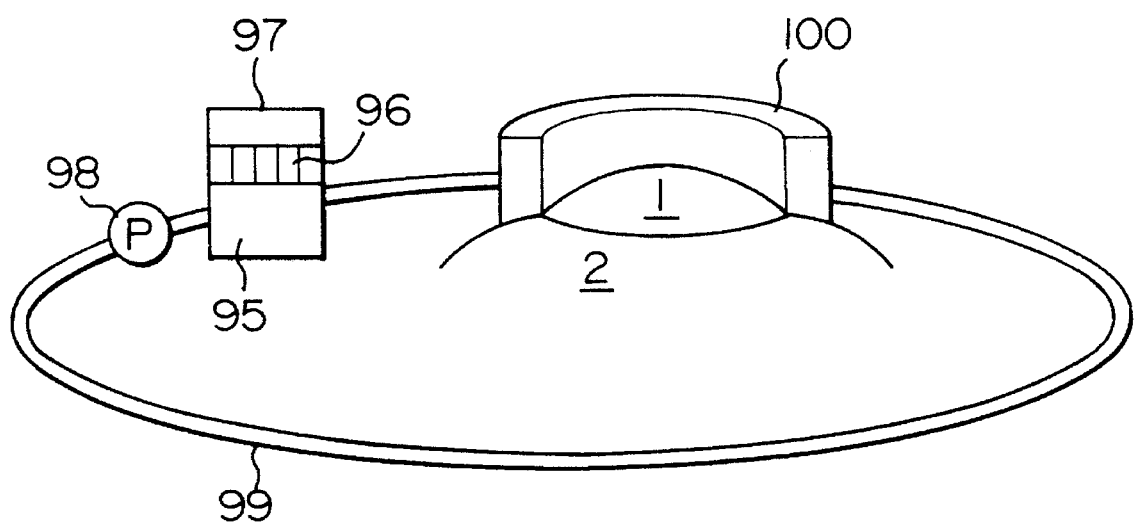
FIG. 17 is a schematic view of an embodiment in which a peripheral portion of the cornea is cooled by a cooling fluid during an eye cornea operation.

FIG. 17 shows a cornea cooling apparatus of a simple construction in which a cooling fluid cooled by a Peltier element is circulated through an annular cooling device placed on a peripheral portion of the cornea. The fluid stored in a tank 95 is cooled by the Peltier element 96, and is circulated by a pump 98 through the hollow, annular cooling device 100 via a tube 99. 97 denotes a heatsink for cooling a heat-generating portion of the Peltier element. In this embodiment, also, the irradiation of an excimer laser can be effected while cooling the cornea.

CAPABILITY OF EXPLOITATION IN INDUSTRY

According to the present invention, in the surgical operation on the cornea of the eye by the use of the ultraviolet laser, particularly the excimer laser, the treatment effect can be achieved with less side effects.

I claim:

1. A method of operating a cornea of an eye with an ultraviolet laser beam, comprising the steps of:
    cooling the cornea, which is to be ablated, to suppress a photochemical thermal effect of the laser beam and also to lower the activity of cells of the cornea;

sprinkling or spraying a liquid medicine, having such effects as cornea remedy, cure promotion and resolution, onto the cornea at predetermined times before and after and in between ablating the cornea with the laser beam;

separating an epithelium of the cornea; and removing the excess liquid medicine on the cornea and applying the laser beam to ablate the cornea.

2. A cornea operating method according to claim 1, further comprising the step of fixing the eye in a stationary condition at least during the ablating step by fixing means held in contact with the sclera around the cornea of the eye.

3. A cornea operating method according to claim 2, wherein said ultraviolet laser beam is generated by an excimer laser.

4. A cornea operating method according to claim 1, wherein said ultraviolet laser beam is generated by an excimer laser.

5. A cornea operating method according to claim 1, wherein said laser beam is intermittently pulsed during the ablation step, and the timing of irradiation of said laser beam, the timing of supply of said liquid medicine and the timing of removal of said liquid medicine are controlled so that the supply of said liquid medicine onto the cornea and the removal of said liquid medicine from the cornea is effected between the pulses.

6. A cornea operating method according to claim 1, wherein the epithelium of the cornea is separated by contacting a disk, which has a lower surface defined by a curved surface conforming in curvature to the cornea and has a cutting blade mounted on said lower surface, with the cornea, and then by rotating said disk.

7. A cornea operating method according to claim 1, wherein the cornea is cooled by a cooling member having Peltier elements incorporated therein, and electric current flowing through said Peltier element is controlled in accordance with the temperature of said cooling member detected by a sensor, thereby cooling the cornea to a predetermined temperature.

8. A cornea operating method according to claim 1, wherein the liquid medicine is instilled on the eye and an internal medicine is administered one week before the ablating the cornea.

9. A cornea operating method according to claim 8, wherein said liquid medicine is a solution of a mixture of oxygltatione, salts, buffer salts, glucose, RINDERON, an antibiotic agent selected from the group consisting of TARIVID, Sikon, and Toki; and said internal medicine for administration is an antiphlogistic selected from a group consisting of TATION, steroid, and INDACINE.

10. A cornea operating method according to claim 1, further comprising the step of administering a medicine, having such effects as cornea remedy, cure promotion, pain easing, infection prevention and resolution, after the cornea ablation.

11. A cornea operating method according to claim 10, wherein said medicine is composed of a mixture of NEO-MEDROL EE ointment, an antibiotic agent selected from the group consisting of TARIVID, INDACINE TATION, Sikon plus Toki, neurotensin and fibronectin plus EGF (Epidermal Growth Factor).

12. An apparatus for operating a cornea of an eye comprising:

an ultraviolet laser beam source for ablating the cornea;

control means for controlling an ultraviolet laser beam emitted from the laser beam source;

an optical system for guiding the laser beam to the cornea; and means for cooling the cornea;

means for sprinkling or spraying a liquid medicine onto the cornea; and means for removing the liquid medicine supplied onto the cornea.

13. A cornea operating apparatus according to claim 12, wherein said ultraviolet laser beam source is an excimer laser.

14. A cornea operating apparatus according to claim 12, further comprising a microcamera for picking up an image of the cornea, the microcamera being adapted for connection to a television monitor.

15. A cornea operating apparatus according to claim 12, further comprising fixing means adapted to rest on a sclera around the cornea of the eye for fixing the eye in a stationary condition.

16. A cornea operating apparatus according to claim 15, wherein said fixing means comprises a number of claws arranged in a ring-like manner for engaging the sclera.

17. A cornea operating apparatus according to claim 14, wherein said fixing means comprises an annular suction tube having a number of through holes for resting on the sclera, wherein said suction tube is kept under negative pressure.

18. A cornea operating apparatus according to claim 17, wherein said fixing means comprises a hollow cylindrical fixing tube and said suction tube is mounted on an inner periphery of said fixing tube at a lower end thereof; said cooling means comprises a ringshaped cooling pipe mounted on the inner periphery of said fixing tube at an upper end thereof and has a number of downwardly-directed, cooling fluid-injecting nozzles; and said optical system applies the laser beam to the cornea from an upper side of said fixing tube through a central space in said fixing tube.

19. A cornea operating apparatus according to claim 18, wherein a lid having laser beam-transmitting properties is attached to an upper open end of said fixing tube, and a suction pipe for discharging the cornea cut by the laser beam is connected to said fixing tube.

20. A cornea operating apparatus according to claim 15, wherein said fixing means comprises a fixing ring supported for upward and downward movement, and a number of claws projecting downwardly from said fixing ring; said cooling means comprises a ring-shaped cooling pipe disposed above said fixing ring coaxially therewith, said cooling pipe having a number of downwardly-directed, cooling medium-injecting nozzles; and said optical system including means for guiding the laser beam to the cornea through spaces surrounded respectively by said cooling pipe and said fixing ring.

21. A cornea operating apparatus according to claim 20, wherein a shut-off valve is mounted on a pipe connecting said cooling pipe to a cooling fluid source, and further comprising a controller for controlling said shut-off valve, where said shut-off valve is closed when said laser beam is irradiated and said shut-off valve is open when said laser beam is not irradiated.

22. A cornea operating apparatus according to claim 12, further comprising a sensor for detecting a temperature of said cooling means, and a temperature control device responsive to a signal from said sensor for controlling the temperature of said cooling means to a predetermined temperature.

23. A cornea operating apparatus according to claim 12, wherein said cooling means includes a flowing cooling medium.

24. A cornea operating apparatus according to claim 12, wherein said cooling means includes a Peltier element.

25. A cornea operating apparatus according to claim 12, further comprising a second cooling means having Peltier elements arranged in an annular manner around said cooling means and adapted for contacting a sclera around the cornea and a peripheral portion of the cornea; pressurized gas-injecting nozzles for clearing the liquid medicine from the cornea; and a cylindrical member bonded coaxially to an upper surface of said Peltier elements, wherein the sprinkling or spraying means comprises liquid spraying nozzles and the liquid medicine removing means comprises liquid medicine suction holes formed at an inner wall surface of the cylindrical member bonded coaxially to an upper surface of said Peltier elements; and wherein the laser beam is adapted to be applied to the cornea from an upper side of said cylindrical member through a central portion of said cylindrical member.

26. A cornea operating apparatus according to claim 12, further comprising an annular cooling block of a thermally-conductive material having a central bore and a lower surface adapted for contacting a peripheral portion of the cornea, a circular array of Peltier elements having a central bore mounted on said cooling block, and an annular heatsink having a central bore mounted on said Peltier elements; wherein the laser beam is adapted to be applied to the cornea from an upper side of said heatsink through the central bores of said heatsink, said Peltier elements, and said cooling block.

27. A cornea operating apparatus according to claim 26, wherein said heatsink includes fins provided on an upper portion of said Peltier elements.

28. A cornea operating apparatus according to claim 12, wherein said cooling means comprises a plate of a thermally-conductive material having a lower surface adapted to conform to a curvature of the cornea, a Peltier element mounted on an upper surface of said plate, and a heatsink mounted on an upper surface of said Peltier element, said plate having a hole formed through a central portion thereof for passing the laser beam therethrough.

29. A cornea operating apparatus according to claim 12, wherein said cooling means comprises a cooling block having Peltier elements and a lower surface thereof adapted to a curvature of the cornea, a heatsink mounted on an upper surface of said Peltier elements, said heatsink and said cooling block having bores formed respectively through central portions thereof for passing the laser beam therethrough.

30. A cornea operating apparatus according to claim 12, further comprising an annular outer tube adapted for resting on a sclera around the cornea and a peripheral portion of the cornea, and around said cooling means, and an inner tube positioned within the outer tube, said outer tube comprising a cooling block of a thermally-conductive material having a lower surface shaped to contact the sclera and the peripheral portion of the cornea, and has a negative pressure-acting suction chamber open to said lower surface, Peltier elements mounted on said cooling block in an annular manner, and an annular heatsink mounted on said Peltier elements; said inner tube having a liquid medicine reservoir of a thermally-conductive material, which has a lower surface conforming with the cornea curvature, the lower surface having a number of liquid medicine discharge holes formed therethrough, and a liquid medicine supply hole, wherein said cooling means comprises an additional Peltier element mounted on said liquid medicine reservoir and a heatsink mounted on said additional Peltier element; and wherein the liquid medicine removing means comprises a liquid medicine suction hole formed in said cooling block of said outer tube.

31. An apparatus for operating a cornea of an eye comprising:

an ultraviolet laser beam source for ablating the cornea;

control means for controlling an ultraviolet laser beam emitted from the laser beam source;

an optical system for guiding the laser beam to the cornea; and a device for cooling the cornea, the cooling device comprising:

a cooling member having a bottom wall and a cylindrical side wall, the bottom wall having a curvature conforming to a curvature of the cornea; and a cooling means for cooling at least the cooling member.

32. A cornea operating apparatus according to claim 31, further comprising an outwardly-projecting flange on an outer periphery of the bottom wall and maintaining means on a lower surface of the flange for resting on a sclera portion of the eye to fix the cooling member relative to the eye.

33. A cornea operating apparatus according to claim 31, wherein the cooling means includes a casing and an infeed port and a discharge port through which a cooling medium flows.

34. A cornea operating apparatus according to claim 31, wherein the cooling member has an upper chamber, an intermediate chamber, and a lower chamber that forms the bottom wall, the bottom wall having discharge ports, wherein a liquid medicine is injected into the lower chamber and discharged through the discharge ports, wherein the cooling means comprises a Peltier element, the intermediate chamber holding the Peltier element, and wherein the upper chamber comprises a heatsink.

35. A cornea operating apparatus according to claim 31, wherein the cooling member comprises a cooling block of thermally conductive material for contacting the cornea, the cooling means comprising Peltier elements mounted on the cooling block and a heat sink mounted on the Peltier elements.

36. A cornea operating apparatus according to claim 31, wherein the cooling member comprises a cooling block of a thermally-conductive material for contacting the cornea, the cooling means comprising a Peltier element mounted on the cooling block and cooling fins mounted on the Peltier element.

* * * * *